United States Patent
James et al.

(10) Patent No.: US 9,936,981 B2
(45) Date of Patent: Apr. 10, 2018

(54) ANCHOR DEVICE FOR ANCHORING AN ELONGATED ROD TO THE SPINE

(71) Applicant: Spine Wave, Inc., Shelton, CT (US)

(72) Inventors: Anthony James, Bartlett, TN (US); Tawney Schwarz, Orange, CT (US)

(73) Assignee: SPINE WAVE, INC., Shelton, CT (US)

(*) Notice: Subject to any disclaimer, the term of this patent is extended or adjusted under 35 U.S.C. 154(b) by 0 days.

(21) Appl. No.: 15/404,622

(22) Filed: Jan. 12, 2017

(65) Prior Publication Data
US 2017/0128106 A1    May 11, 2017

Related U.S. Application Data

(63) Continuation of application No. 13/942,823, filed on Jul. 16, 2013, now Pat. No. 9,545,279, which is a continuation of application No. 12/186,661, filed on Aug. 6, 2008, now Pat. No. 8,491,639.

(51) Int. Cl.
*A61B 17/70* (2006.01)
*A61B 17/86* (2006.01)

(52) U.S. Cl.
CPC ...... *A61B 17/7043* (2013.01); *A61B 17/7035* (2013.01); *A61B 17/7076* (2013.01); *A61B 17/8605* (2013.01)

(58) Field of Classification Search
CPC .................. A61B 17/7037; A61B 17/8605
See application file for complete search history.

(56) References Cited

U.S. PATENT DOCUMENTS

| 6,887,242 B2 | 5/2005 | Doubler et al. |
| 7,087,057 B2 | 8/2006 | Konieczynski et al. |
| 2001/0001119 A1 | 5/2001 | Lombardo |
| 2003/0153911 A1 | 8/2003 | Shluzas |
| 2005/0070899 A1 | 3/2005 | Doubler et al. |
| 2005/0283157 A1 | 12/2005 | Coates et al. |
| 2006/0052786 A1 | 3/2006 | Dant et al. |
| 2006/0084981 A1 | 4/2006 | Shluzas |
| 2007/0032849 A1 | 2/2007 | Schlapfer et al. |
| 2007/0093832 A1 | 4/2007 | Abdelgany |
| 2007/0118123 A1 | 5/2007 | Strausbaugh et al. |
| 2008/0003054 A1 | 1/2008 | Fan |
| 2008/0021465 A1 | 1/2008 | Shadduck et al. |

(Continued)

OTHER PUBLICATIONS

WCL Company, Spring Washers: Description & Design Considerations; p. 5; 2005-2006.

*Primary Examiner* — Jan Christopher Merene
*Assistant Examiner* — Atiya Mahmud
(74) *Attorney, Agent, or Firm* — Hoffmann & Baron, LLP

(57) ABSTRACT

A spinal fixation system includes a rod and anchor devices that include a bone engaging fastener having a head defining a spherical socket. A ball insert is placed within the socket and rotated so that the ball insert is juxtaposed with the socket. The anchor device further includes a yoke defining a yoke channel for receiving the rod and a stem engaged to the ball insert captured within the socket. A sleeve disposed between the yoke channel and the fastener head supports the rod. A set screw is operable to clamp the rod against the sleeve and draw the insert into engagement within the socket. A friction element in the form of a wave spring is disposed between the yoke and the fastener head is configured to releasably retain the yoke in at least one discrete position relative to the fastener.

7 Claims, 14 Drawing Sheets

(56) References Cited

U.S. PATENT DOCUMENTS

| | | |
|---|---|---|
| 2008/0119857 A1 | 5/2008 | Potash et al. |
| 2008/0119858 A1 | 5/2008 | Potash |
| 2008/0312692 A1 | 12/2008 | Brennan et al. |
| 2009/0118772 A1 | 5/2009 | Diederich et al. |
| 2010/0030279 A1 | 2/2010 | Flynn et al. |
| 2010/0036417 A1 | 2/2010 | James et al. |
| 2011/0046684 A1 | 2/2011 | Abdelgany et al. |

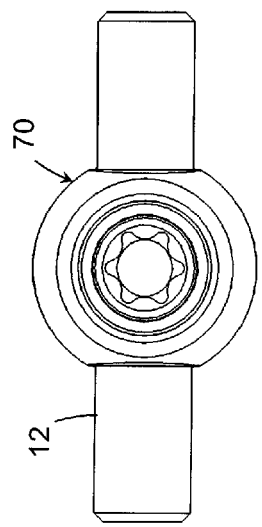
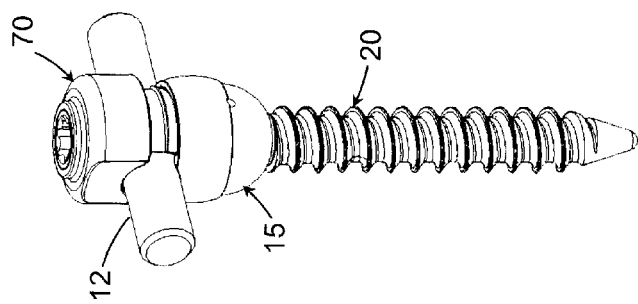

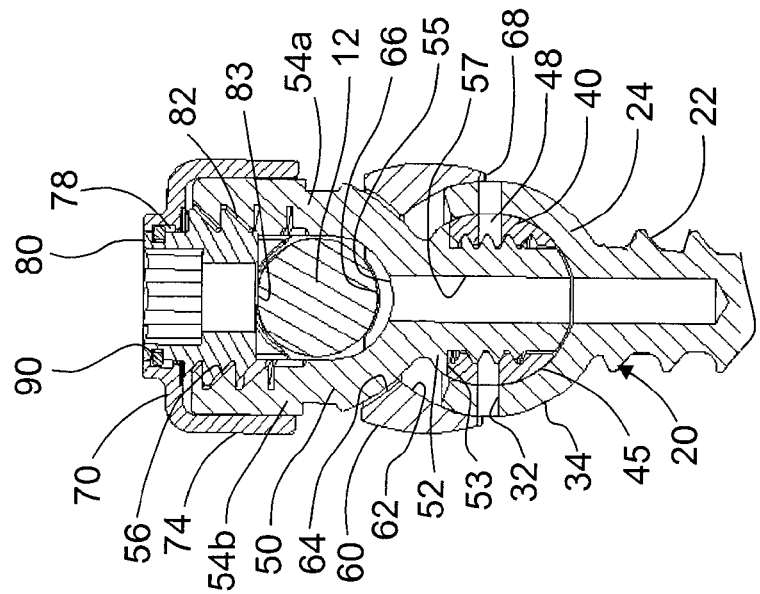
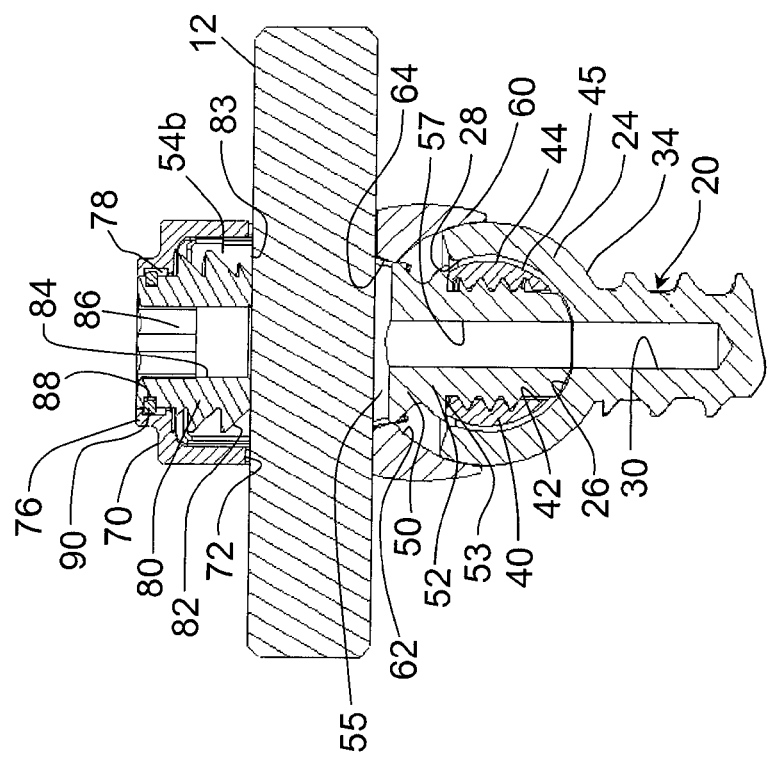

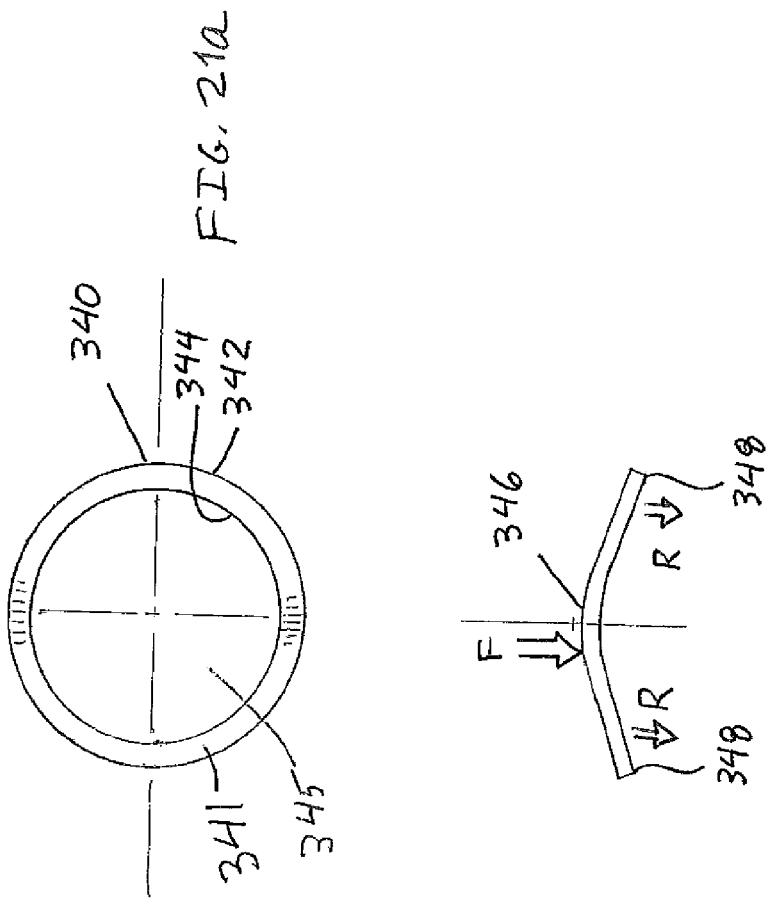
FIG. 21a
FIG. 21b
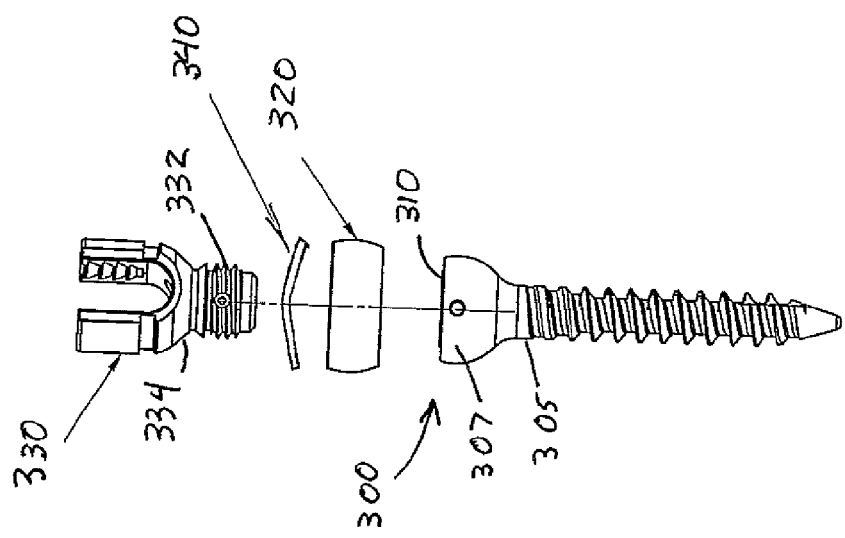
FIG. 20

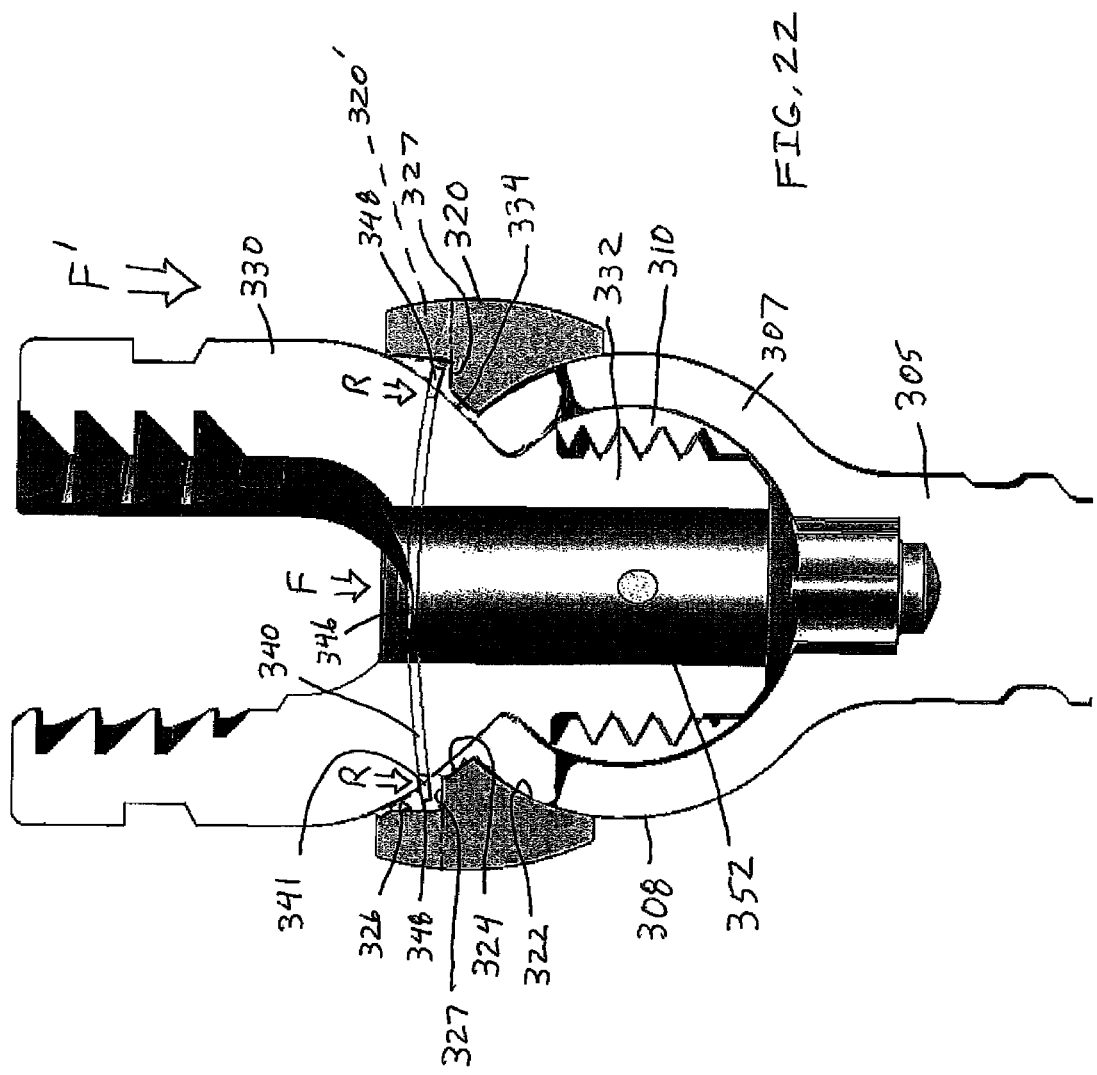

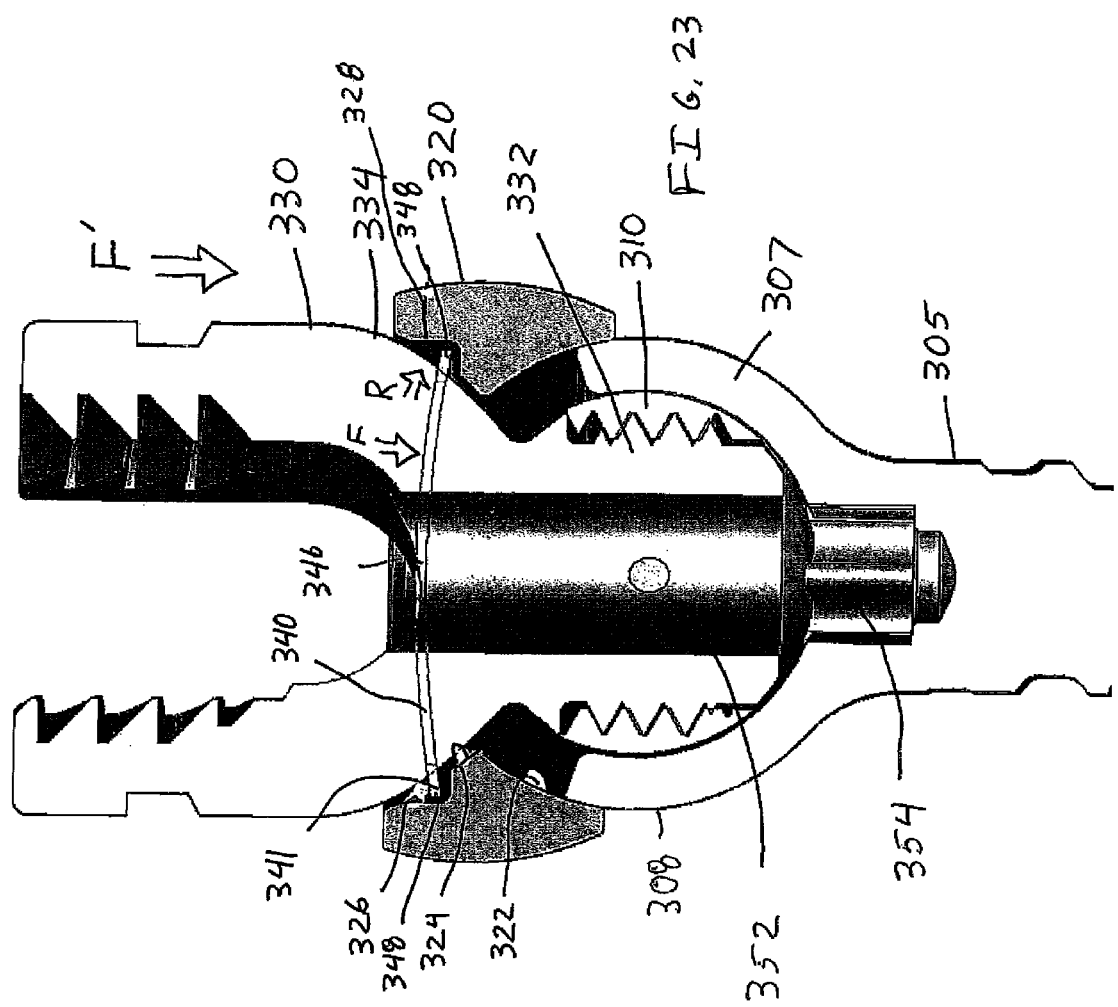

ANCHOR DEVICE FOR ANCHORING AN ELONGATED ROD TO THE SPINE

CROSS REFERENCE TO RELATED APPLICATIONS

This application is a continuation of U.S. application Ser. No. 13/942,823, filed on Jul. 16, 2013, now U.S. Pat. No. 9,545,279, which is a continuation of U.S. application Ser. No. 12/186,661, filed on Aug. 6, 2008, now U.S. Pat. No. 8,491,639, the entire contents of which are herein incorporated by reference in their entirety.

BACKGROUND OF THE INVENTION

The present disclosure relates to spinal fixation systems and particularly to an anchor device that incorporates multi-axial fixation to the spine.

Several techniques and systems have been developed for correcting and stabilizing injuries to or malformation of the spine. In one type of system, an elongated member such as a bendable rod is disposed longitudinally along a length of the spine, spanning two or more vertebral levels. In certain applications, the rod is bent to correspond to the normal curvature of the spine in the particular region being instrumented, such as the normal kyphotic curvature of the thoracic region or the lordotic curvature of the lumbar region. In accordance with such a system, the rod is engaged to various vertebrae along a length of the spinal column by way of a number of anchor devices that utilize a variety of fixation elements configured to engage specific portions of the vertebra and other bones. For instance, one such fixation element is a hook that is configured to engage the laminae of the vertebra. Another very prevalent fixation element is a screw that can be threaded into various parts of the vertebrae or other bones.

Early rod-type spinal fixation systems incorporated anchor devices that permitted very limited relative orientations of the rod relative to the fixation element. As these system evolved, various degrees of freedom of relative orientation were integrated into the system. For instance, in one system a bone screw may be engaged to the spinal rod at a range of planar angles. This so-called variable angle screw allows pivoting of the bone screw in a single plane parallel to the plane of the spinal rod. One goal achieved by the variable angle screw is that the surgeon can apply vertebral fixation elements to the spine in more appropriate anatomic positions.

Another rod-type fixation system utilizes fixation elements having a body that defines a slot within which the spinal rod is received. The slot includes a threaded bore into which a threaded plug is engaged to secure the rod within the body of the fixation element. One benefit of this type of fixation element is that the fixation element may be positioned directly beneath the elongated rod, thereby reducing the overall bulkiness of the implant construct and minimizing trauma to the surrounding tissue.

On the other hand, these so-called "open back" fixation elements are capable only of pivoting about the spinal rod to achieve variable angular positions relative to the rod. While this limited range of relative angular positioning is acceptable for many spinal pathologies, many other cases require more creative orientation of a bone fastener relative to a spinal rod. Certain aspects of this problem are addressed by some prior multi-axial or poly-axial screws that are capable of various three-dimensional orientations with respect to the spinal rod. One type of poly-axial screw design, shown in U.S. Pat. No. 6,537,276 to Metz-Stavenhagen et al., includes a spherical projection on the top of the bone screw. An internally threaded receiver member pivotally supports the bone screw and a spinal rod on top of the spherical projection. An inner set screw is tightened into the receiver member to press the spinal rod against the spherical projection to accommodate various angular orientations of the bone screw relative to the rod. A similar multi-axial screw is disclosed in U.S. Pat. No. 5,466,237 to Byrd et al., except an outer nut is provided to secure the rod against the head of the bone screw.

In another approach shown in U.S. Pat. No. 4,946,458 to Harms et al., a spherical headed bone screw is supported within separate halves of a receiver member. The bottoms of the halves are held together by a retaining ring. The top of the receiver halves are compressed about the bone screw by nuts threaded onto a threaded spinal rod. One detriment of this system is that the spinal rod must be threaded in order to accept the compression nuts, which has a tendency to weaken the spinal rod in the face of severe spinal loads. Harms et al. also describes in U.S. Pat. No. 5,207,678 another multi-axial pedicle screw wherein a compression member is provided between the rod and the head of the screw to exert a force on the screw head to lock the screw against the inner spherical surface of the receiver member.

Yet another approach is illustrated in U.S. Pat. No. 5,797,911 to Sherman et al., in which a U-shaped holder is provided that receives a bone fastener topped with a crown member. The holder accommodates a rod in a channel above the crown member and a compression member above the rod. The compression member presses on the rod and crown member to lock the fastener against the holder in any of a number of angles in three dimensions with respect to the rod. Another system shown in U.S. Pat. No. 5,733,285 to Errico et al., includes a holder having a tapered and colleted portion into which a bone fastener head is inserted. A sleeve is provided that translates down around the colleted portion to crush lock the colleted portion around the head of the bone fastener. This apparatus is bulky and difficult to manipulate given the external sliding locking mechanism. It is further dependent on the fit of the external sleeve and the relative strength of the collet and its bending and crushing portions for secure locking of the bone fastener head.

A difficulty that appears to be associated with many of the known poly-axial bone screws is that as a result of the poly-axial freedom of movement, the U-shaped rod holder tends to 'flop" relative to the bone fastener. In U.S. Pat. No. 7,087,057, Konieczyinski et al. attempt to address this issue by including a snap ring to provide sufficient friction between the head of the bone fastener and the rod holder so as to hold a relative position therebetween before the holder and fastener are locked together in use.

There remains a need for a multi-axial or poly-axial fixation system for use with a spinal fixation system that is simple to construct yet strong enough to withstand harsh spinal loads. There is a further need for a fixation system that includes features to temporarily hold the rod holder in position relative to the bone fastener while still allowing manipulative movement by the surgeon.

SUMMARY OF THE INVENTION

The present disclosure contemplates a spinal fixation system that incorporates multi-axial fixation characteristics in a low-profile, easy to construct anchor device. The system includes an elongated member, such as a spinal rod, that extends between spinal segments. A series of anchor devices anchor the rod to the spinal segments, with at least some of the anchor devices providing multi-axial fixation. In one embodiment, the multi-axial anchor device includes a bone engaging fastener that is adapted to engage a portion of the spine. In one specific embodiment, the fastener is a bone screw adapted to be threaded into the pedicle of a vertebra.

Connection to the spinal rod is provided by way of a yoke that is free to swivel relative to the fastener. The yoke defines a channel between opposing arms of the yoke, with the channel configured to snugly seat the rod therein. A sleeve is provided that fits about an upper portion of the head of the bone engaging fastener. This upper portion provides a spherical surface to interface with a spherical lower cavity of the sleeve so that the sleeve may adapt a range of spherical angles relative to the bone engaging fastener as necessary to accommodate the position of the spinal rod relative thereto.

In a particular configuration, a friction member in the form of a spring element is disposed between the yoke and the outer sleeve disposed over the head of the fastener. The spring element is configured to releasably retain the yoke in at least one pre-determined position relative to the fastener. In one specific embodiment, the spring element is in the form of a wave spring that sits within a recess or cavity formed in the outer sleeve. The inner diameter of the wave spring engages a lower surface of the yoke so that a downward force applied to the yoke produces a force exerted by the wave spring against the outer sleeve. This force creates a static friction force that resists movement of the yoke relative to the sleeve, and ultimately relative to the fastener.

Thus, in one feature, the spring element is configured so that slightly tightening the yoke into the ball insert generates a downward force on an apex of the wave spring configuration. The amount of downward force dictates the amount of force exerted by the spring element against the outer sleeve, which directly correlates to the static friction force that resists movement of the yoke. Preferably the static friction force is sufficiently high to firmly hold the yoke in its position relative to the fastener, but sufficiently low to allow the surgeon to manually manipulate the yoke to a new position as required when building the fixation construct in situ.

One benefit of the device disclosed herein is that it provides for solid anchoring between a spinal rod and a bone engaging fastener at variable spherical angles. A further benefit is that a common clamping element is provided to clamp the spinal rod and fix the angular position of the anchor device.

Yet another benefit resides in one aspect of the anchor device that reduces the overall prominence and profile of the components of the device. A still further benefit is that the relative angular position of the components may be temporarily held during implantation or in anticipation of engagement with a prepared spinal rod. Other benefits can be discerned from the following written description and accompanying figures.

DESCRIPTION OF THE FIGURES

FIG. 2 is a side perspective view of an anchor device according to one embodiment for use in the fixation system shown in FIG. 1.

FIG. 3 is a top plan view of the anchor device shown in FIG. 2.

FIG. 4 is a side cross-sectional view of the anchor device of FIG. 2.

FIG. 5 is a longitudinal cross-sectional view of the anchor device illustrated in FIG. 2 along the longitudinal axis of the elongated member.

FIG. 20 is an exploded view of an anchor device according to a further embodiment incorporating a spring element for temporarily holding the yoke in a position relative to the fastener of the anchor device.

FIGS. 21a, 21b are top and side views of the spring element incorporated into the anchor device shown in FIG. 20

FIG. 22 is a cross-sectional view of the assembled anchor device shown in FIG. 20 showing the reaction force generated by the spring element between the yoke and the outer sleeve.

FIG. 23 is a cross-sectional view of the assembled anchor device with an alternative reaction force generated by the spring element.

DESCRIPTION OF THE EMBODIMENTS

Figure 1:
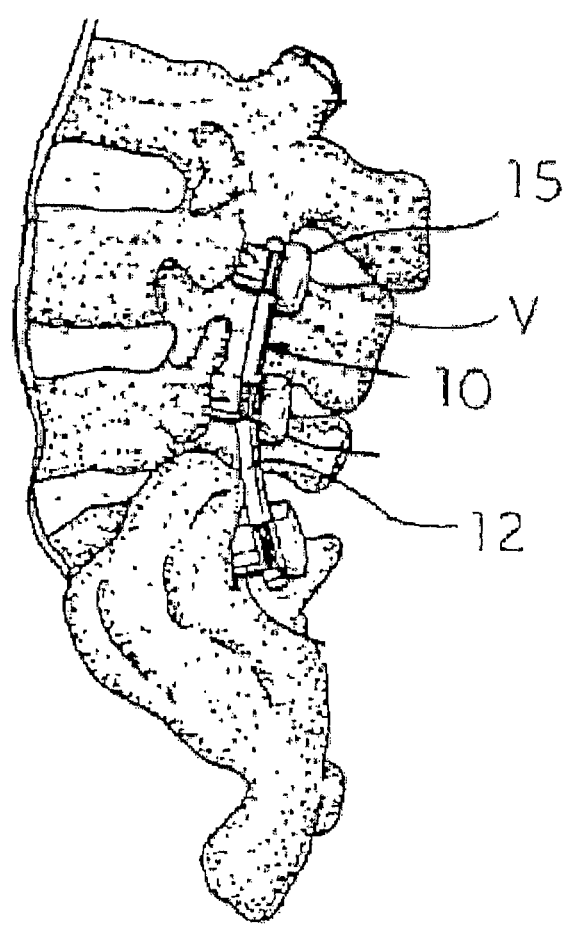
FIG. 1 is a transverse view of a portion of a spine with a fixation system utilizing an elongated members engaged between successive vertebrae.

Reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present disclosure contemplates a spinal fixation system, such as the system 10 depicted in FIG. 1. As is known in the art, the fixation system 10 spans between successive vertebrae of the spine. An elongated member, such as rod 12, extends along the length of the spine and provides an anchor point for connecting each vertebra to the rod. The rod is typically contoured to approximate the normal curvature of the spine for the particular instrumented spinal segments. Anchor devices 15 are provided for connecting the vertebral segments to the rod. These anchor devices may include hooks, bolts, screws or other means for engaging a vertebra. For the purposes of the present discussion, the anchor device 15 includes a bone engaging fastener 20 which is a bone screw, as shown in FIG. 2. The bone screw 20 includes a threaded shank 22 configured for threaded engagement within a portion of a vertebra. In a specific example, the shank is configured for engagement within the pedicle of a vertebra.

The bone engaging fastener or screw 20 further includes a head 24 by which the screw, and ultimately the vertebra, is anchored to the spinal rod 12. In accordance with one feature, the head 24 defines a spherical socket 26 with a socket opening 28 facing the rod, as shown in FIGS. 4-5. The bone screw 20 further defines a central bore 30 intersecting the socket and extending part way into the threaded shank 22. A transverse bore 32 extends through the head 24 and across the socket, as best seen in FIG. 5. The function of the bores 30 and 32 are discussed herein. The head 24 includes a spherical outer surface 34.

It can be appreciated from considering FIGS. 4-5 that the spherical head 24 of the bone screw is more than simply hemi-spherical. In other words, the spherical socket 28 subtends a spherical angle of greater than 180° so that socket opening 28 is defined at a chord of the spherical socket. The planar diameter of the opening 28 at the chord is less than the inner diameter of the socket. In a specific embodiment, the spherical head subtends a spherical angle of about 240° and the planar chordal diameter of the socket opening 28 is about 90% the spherical diameter of the socket. It can thus be appreciated that a ball element of about the same spherical diameter disposed within the socket will be retained within the socket, unable to pass through the socket opening. It will be appreciated from the following discussion that a smaller planar chordal diameter will reduce the range of angulation of the articulating components of the anchor device.

Figure 6:
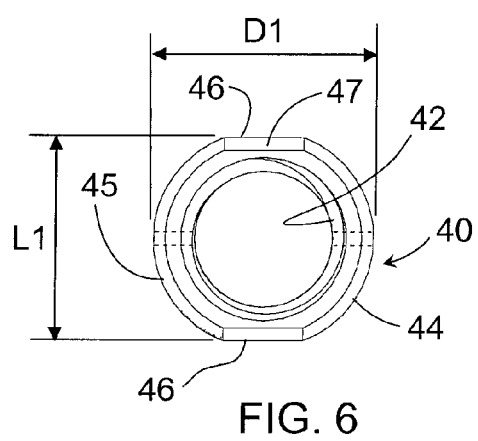
FIG. 6 is a top plan view of a ball insert element of the anchor device shown in FIG. 2.
Figure 7:
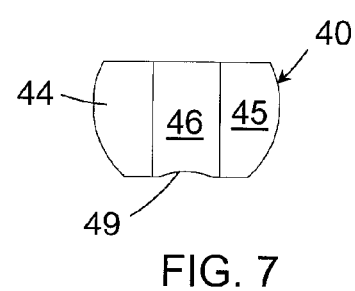
FIG. 7 is a side elevational view of the ball insert shown in FIG. 6.

Of course, a ball element that is too large to pass through the opening 28 cannot be readily inserted into the socket 26. The present device addresses this matter by a ball insert element 40, illustrated in detail in FIGS. 6-7. The ball insert 40 defines a central threaded bore 42 that is provided for connection to a yoke component 50, as described in more detail herein. The ball insert is generally in the form of a truncated sphere, whereby the outer surface 44 of the ball insert includes a spherical surface 45 that is sized to closely approximate the spherical socket 26, as shown in FIG. 5. Thus, spherical surface 45 defines an outer spherical diameter $D_1$, that is slightly less than the interior diameter of the spherical socket 26, but greater than the diameter of opening 28. As seen more particularly in FIG. 8b, the ball insert 40 is further formed to have a cylindrical portion defined by curved surfaces 46. The curved surfaces 46 of cylindrical portion define an outer diameter $D_2$ about axis A as depicted in FIG. 8b. Axis A in one arrangement is formed to be generally perpendicular to the axis of the central threaded bore 42. In accordance with one aspect the maximum diameter $D_2$ is slightly less than the planar chordal diameter of socket opening 28 (FIG. 8a) and defines an insert dimension for placing the ball insert 40 into the socket 26 as will be defined. While curved surfaces 46 are preferably formed to define a cylindrical insert dimension $D_2$, it should be appreciated that other configurations may be considered, such as one or more flattened outer surfaces, provided that a maximum insert dimension such as diameter $D_2$ is formed less than the maximum dimension of the socket opening 28.

Figure 8A:
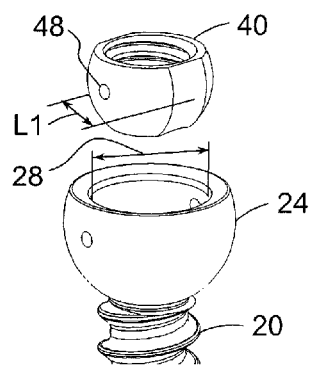
FIGS. 8a-8f are side perspective views of a sequence of assembly of the components of the anchor device shown in FIG. 2.
Figure 8B:
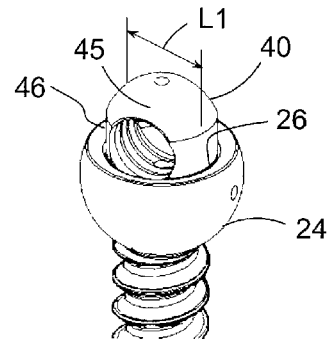
Figure 8C:
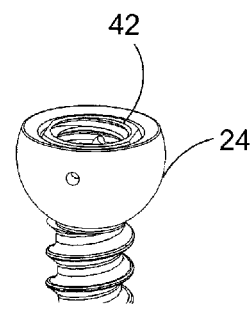

The benefit of this configuration for the ball insert 40 can be readily appreciated upon consideration of the sequence in FIGS. 8a-8c depicting insertion of the ball insert 40 into the socket 26 of the bone screw 20. As shown in FIG. 8b, the ball insert 40 is rotated at least 90° so that the insert dimension $D_2$ with curved surfaces 46 is aligned to pass through planar chordal opening 28 and into the socket 26. The insert dimension $D_2$ is oriented so that axis A of ball insert 40 is essentially aligned along the axis of the bone screw. The depth of the socket 26 is sufficient to fully receive the rotated ball insert 40 so that the spherical surface 45 exposed in the view of FIG. 8b is within the socket. Then, in the final step shown in FIG. 8c, the ball insert 40 is further rotated at least 90° so that the threaded bore 42 faces upward through the socket opening 28. In this position, the spherical surface 45 of the ball insert is juxtaposed with the interior of the spherical socket 26, as shown in FIG. 5, and the ball insert 40 is captively retained in the socket 26 for swivel movement therewithin.

The ball insert 40 is further provided along axis A as seen in FIG. 8a with a transverse bore 48 that may be aligned with the transverse bore 32 in the spherical head 24 of the bone screw, as shown in FIG. 5 and FIG. 8a. As can be seen from the figures, the ball insert is truncated at the top and bottom of the insert. However, the ball insert in this arrangement is not symmetric—i.e., more of the top of the spherical ball is truncated than the bottom of the ball. Further, as a result of the formation of the curved cylindrical surfaces 46, the lower truncated surface has indentations 49 as illustrated in FIG. 7. When the ball 40 is rotated as depicted in FIG. 8b, the indentations 49 may be directed toward the bottom of socket 26 and are not visible through the socket opening.

Returning to FIGS. 4-5, the anchor device 15 further includes a yoke 50 having a threaded stem 52 configured to engage the threaded bore 42 in the ball insert 40. The stem is provided with a shoulder 53 that preferably abuts the ball insert 40 when the stem 52 is fully threaded into the bore 42 of the insert. The yoke 50 includes yoke arms 54a, 54b that define a yoke channel 55 therebetween. The gap between the arms 54a, 54b, and consequently the width of the channel, is sized to closely fit the spinal rod 12, as best seen in FIG. 5. The arms 54a, 54b define internal threads 56 at the upper open end of the yoke 50 for engaging a set screw 80, as described below. A bore 57 passes through the threaded stem 52 that is aligned with the bore 30 in the bone screw when the yoke is mounted on the ball insert.

Figure 8D:
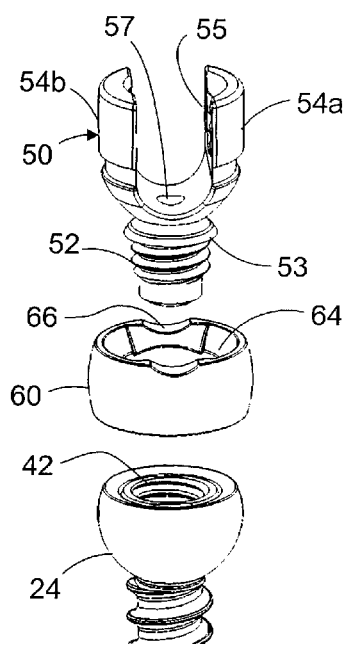
Figure 8E:
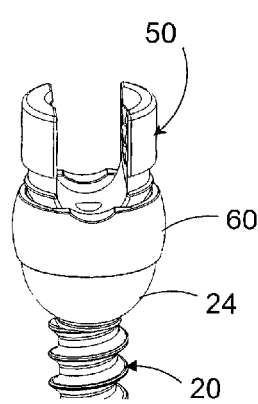
Figure 9:
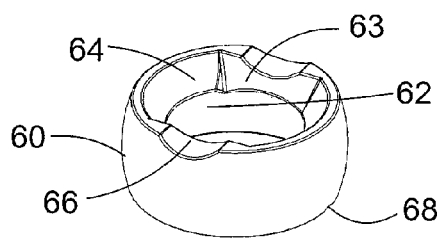
FIG. 9 is a top perspective view of a sleeve component of the anchor device shown in FIG. 2.
Figure 10:
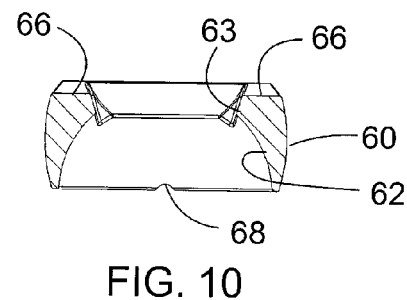
FIG. 10 is a side cross-sectional view of the sleeve shown in FIG. 9.

As shown in FIGS. 8d-8e, a sleeve 60 is interposed between the yoke 50 and the head 24 of the bone screw 20. As further shown in FIGS. 9 and 10, the sleeve 60 defines a lower cavity 62 that has a spherical configuration to substantially match the spherical outer surface 34 of the screw head 24. Sleeve 60 sits on the outer surface 34 for sliding movement thereon, and serves as a clamping element for the rod 12 relative to the yoke as will be described. The sleeve further defines an upper cavity 64 that generally parallels the outer surface of the yoke arms 54a, 54b, as seen in FIG. 5. The upper face of the sleeve 60 defines opposite rod grooves 66 sized to receive the spinal rod 12 therein. The lower face of the sleeve defines opposite notches 68 that are oriented 90° from the rod grooves 66. The notches 68 are arranged to align with the transverse bores 32 and 48 when the anchor device is assembled. The notches and bores are sized to receive retaining pins 155 (FIG. 11) as described in more detail herein. In a preferred arrangement, sleeve 60, is provided with opposing recessed surfaces 63 that engage the arms 54a, 54b of the yoke 50 to key the sleeve 60 to yoke 50 in a manner that allows common swivel movement of the yoke 50 and sleeve 60 relative to the screw head 24.

Figure 11:
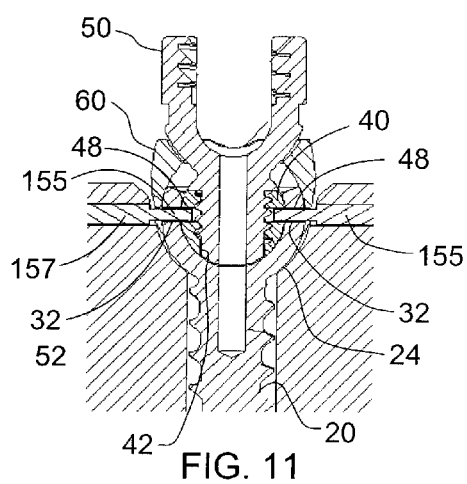
FIG. 11 is a longitudinal cross-sectional view of a fixture with holding pins for holding the position of the ball insert relative to the socket during engagement of the yoke.

As depicted in FIGS. 8d-8e, after the ball insert 40 is properly aligned and captively retained as shown in FIG. 8c, the yoke 50 may engage the insert 40 to form an assembly therewith. In accordance with the preferred manner of assembly of the anchor device 15, the threaded stem 52 of the yoke is extended through the sleeve 60 with the sleeve keying surfaces 63 aligned with the yoke arms 54a, 54b. The threaded stem 52 is then threaded into engagement with the threaded bore 42 of the ball insert. In order to achieve this threaded engagement it is necessary to hold the ball insert 40 as the stem 52 of the yoke is threaded into the bore 42. Thus, in one aspect the ball insert 40 is oriented within the spherical socket 26 so that the transverse bores 48 in the insert are aligned with the transverse bores 32 in the screw head. When the bores are aligned, pins 155 may be pushed therethrough, taking care that the pins do not extend into the threaded bore 42, as illustrated in FIG. 11. Arms 157 of a forceps-like tool may be used to introduce the pins into the bores.

With the pins 155 in position, the sleeve 60 may be placed over the head of the bone screw with the notches 68 aligned with the pins 155. The yoke is then extended through the sleeve with the stem engaging the threaded bore 42 of the ball insert. The pins 155 resist rotation of the ball insert 40 as the stem is threaded into the bore. The yoke 50 is threaded into the ball insert until the shoulder 53 contacts the upper face of the ball insert 40 as shown in FIGS. 4-5.

Figure 12:
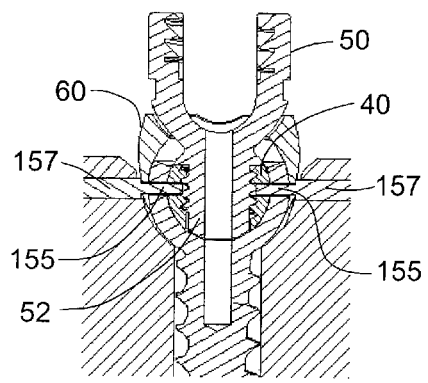
FIG. 12 is a longitudinal cross-sectional view of the fixture with holding pins used to crimp or swage the threads of the yoke to fix the yoke to the ball insert.

In an additional feature, the pins 155 may be used to crimp, swage or deform the threads of the stem 52 of the yoke 50. Thus, the tool arms 157 may be pressed toward each other so that the pins 155 contact the threaded stem 52, as shown in FIG. 12. When the threads are distorted the stem 52 of the yoke cannot back out or unthread from the ball insert 40. Once the yoke and ball insert have been locked together, the pins 155 can be removed. It is understood that this initial assembly of the anchor device, namely the steps shown in FIGS. 8a-8e, occur prior to introduction of the anchor device 15 into the spine, preferably by the supplier. It can also be appreciated that once the yoke 50 is locked with ball insert 40, the ball insert 40 is free to swivel within the fastener socket 26 allowing the yoke attached thereto to freely angulate in multiple directions. Since sleeve 60 is keyed to yoke 50 it likewise freely slides on outer surface 34 of fastener head 24 as the yoke 50 moves, until the anchor device components are locked in use. Furthermore, even though the ball insert 40 is free to swivel within socket 26, once the yoke 50 is attached the insert 40 remains captively retained since the insert 40 will not be able to move to a position where its insert dimension $L_1$ is aligned with the socket opening 28.

Figure 8F:
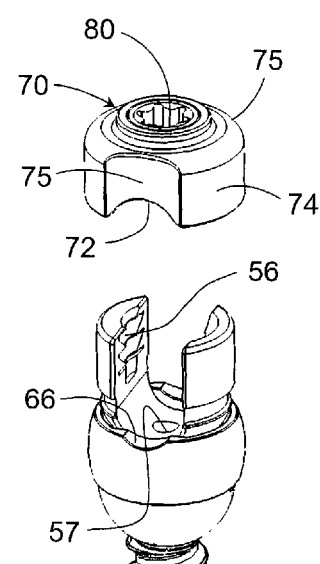
Figure 13:
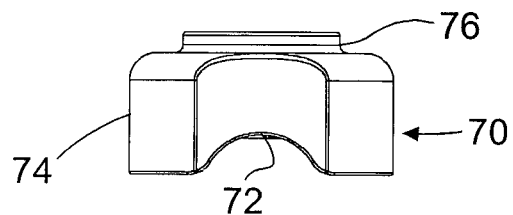
FIG. 13 is a longitudinal elevational view of a cap with set screw of the anchor device of FIG. 2.
Figure 14:
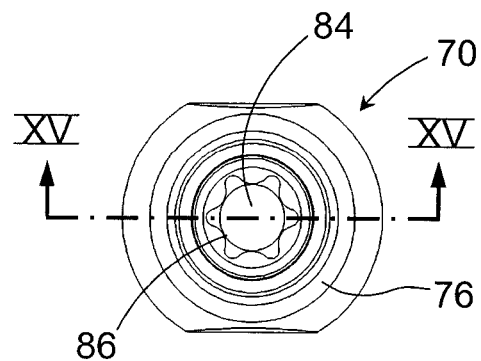
FIG. 14 is a top plan view of the cap shown in FIG. 13.

Returning again to FIGS. 4-5, the assembly of the rod 12 to the fastener 20 is shown. The rod 12 is initially placed between the arms of the yoke 50 to rest on the rod grooves 66 of the sleeve 60. The yoke channel 55 may then be closed, securing the rod within. In accordance with a further feature a cap 70 is fitted over the top of the yoke arms 54a, 54b. The cap 70 as further detailed in FIGS. 13-15, includes a generally cylindrical skirt 74 that fits snugly around the arms 54a, 54b to prevent the arms from splaying outward as set screw 80 is threaded into the arms. The skirt 74 is preferably provided with diametrically opposed flats 75 that correspond to the transverse opening of the yoke channel 55, as best seen in FIG. 8f. The flats 75 define rod grooves 72 that align with, but do not contact, the rod 12 when it is situated within the yoke channel 55.

Figure 15:
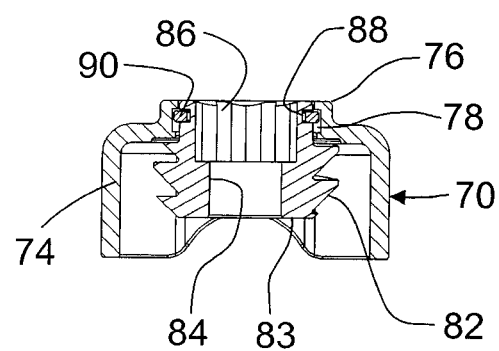
FIG. 15 is a cross-sectional view of the cap of FIG. 14 taken along viewing line XV-XV.

The cap 70 includes an upper boss 76 that defines an enlarged circumferential interior groove 78. This groove is sized to receive a retaining ring or snap ring 90 therein, as seen in FIG. 5 and FIG. 15. The groove is axially enlarged or lengthened so that the snap ring 90 may translate up and down within the boss 76 for reasons explained below.

The set screw 80 is provided with a threaded stem 82 that is configured to engage the internal threads 56 of the yoke arms 54a, 54b. Preferably the threaded engagement between set screw and yoke are in the form of buttress threads, as depicted in FIGS. 4-5. The buttress threads minimize the outward force produced as the set screw is threaded into the yoke. Thus, the use of buttress threads help minimize any splaying of the yoke arms that might otherwise occur when the set screw 80 is threaded tightly into the yoke 50. In addition as shown in FIG. 15, the bottom of the set screw is recessed upwardly of the bottom of the skirt 74 of cap 70. Thus, when cap 70 is placed over the arms 54a, 54b of yoke 50, not only does the close fit of the skirt 74 relative thereto prevent splaying as noted, but skirt 74 also serves as a guide to align the threads 82 of set screw 80 into the threads 56 of the yoke 50, thereby also reducing the risk of disadvantageous cross-threading.

The set screw 80 includes a pressure face 83 that contacts and exerts a securing force against the spinal rod 12. The pressure face 83 as well as the rod surface may exhibit surface features intended to enhance the fixation between set screw and rod, as is known in the art. In particular, a surface roughness may be provided that becomes deformed or cold formed when the set screw is tightened onto the rod. This feature helps prevent the rod from slipping axially (along its length) within the anchor device 15.

The set screw 80 defines a bore 84 therethrough. The upper portion 86 of the bore may be configured to receive a driving tool, such as with hex or TORX surfaces.

Like the cap 70, the set screw 80 defines a circumferential groove 88 (FIG. 4) configured to receive the retaining ring 90 therein. However, unlike the cap groove 78, the groove 88 in the set screw is preferably sized to closely fit the snap ring. Thus, while the snap ring 90 is held by the set screw, the snap ring is free to translate within the elongated cap groove 78. The elongated groove 78 is thus intended to allow the set screw 80 to fully engage the rod 12 while the cap 70 essentially floats by virtue of the snap ring 90 translating within groove 78. Thus, the cap 70 effectively exerts no force on the rod 12 or on the top surface of the yoke 50, even if some contact is made.

Figure 16:
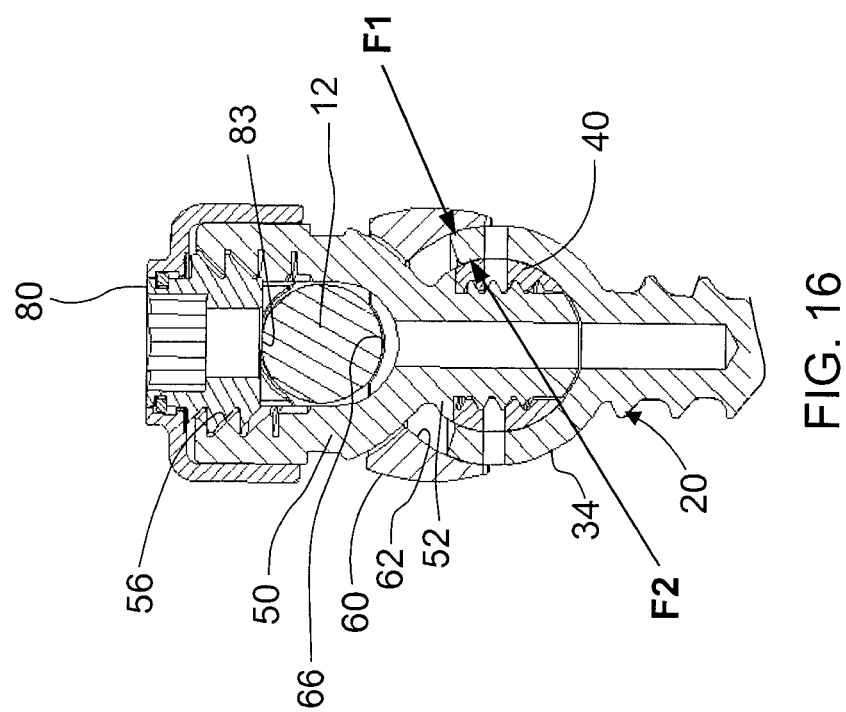
FIG. 16 is a longitudinal cross-sectional view similar to FIG. 5 showing forces generated to lock the components of the anchor device of FIG. 2.

The set screw 80 generates the force that locks the ball insert 40 within the spherical socket 26 at the desired angular orientation, and that further locks the spinal rod 12 within the anchor device 15. In particular, once the anchor device 15 has been fully assembled about the rod 12, as best seen in FIG. 16, the set screw 80 is tightened within the yoke 50. As the screw is tightened, it presses against the rod 12, clamping it between the pressure face 83 of the set screw and the rod grooves 66 in the sleeve 60. As the set screw is driven further into the internal threads 56 of the yoke 50, the set screw pushes the rod 12 downwardly until the lower cavity 62 of the sleeve 60 is firmly engaged to the outer surface 34 of the head 24 of the bone screw generating locking force, F1.

At this point the sleeve 60 and rod 12 can move no further toward the bone screw 20. Therefore, any further tightening of the set screw is reacted by the yoke itself. As the set screw is driven further into the yoke internal threads (i.e., advancing toward the head of the bone screw) this reaction force pulls the yoke upward. While the yoke is pulled upward with continued rotation of the set screw, the stem 52 of the yoke pulls the ball insert 40 upward, owing to the fixed engagement between the yoke stem and the ball insert. As the ball insert is pulled upward, it bears forcefully against the upper face of the spherical socket 26, with a force F2 clamping the socket wall between the sleeve 60 and the ball insert 40 and thereby locking the ball insert 40 and yoke 50 relative to fastener 20. Any tendency of the socket 26 to attempt to gap at the socket opening 28 is resisted by the sleeve 60 that is already in firm engagement about the outer surface 34 of the screw head.

It can thus be appreciated that the entire anchor device can be adjustably secured in a fixed relationship simply by rotation of the set screw 80. As the set screw is threaded into the yoke threads it ensures solid clamping of the bone screw head 24 between the lower cavity 62 of the sleeve 60 and the spherical surface 45 of the ball insert 40, regardless of the angular orientation of the yoke and rod relative to the screw. The rod itself is firmly clamped between the set screw and the lower sleeve. It can further be appreciated that the entire anchor device may be tightened by simply tightening the set screw.

Figure 17:
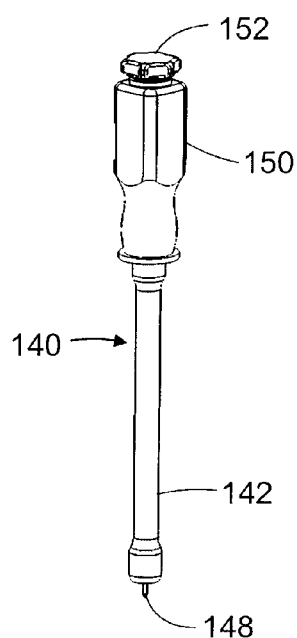
FIG. 17 is a side elevational view of a fastener inserter tool for use with one embodiment of the anchor device of the present disclosure.
Figure 18:
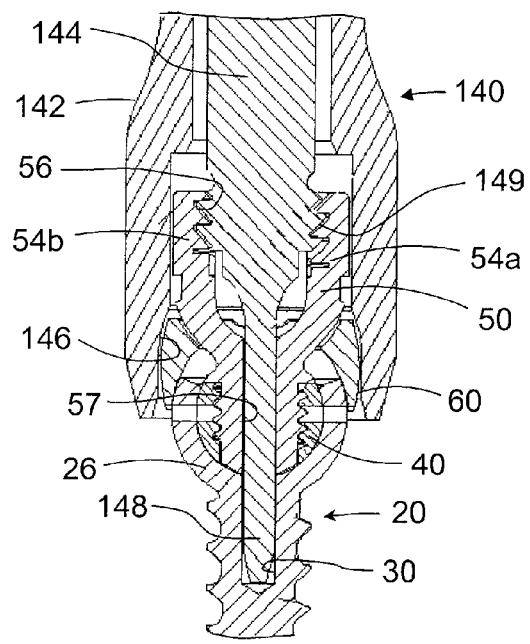
FIG. 18 is a longitudinal cross-sectional view of the fastener inserter tool shown in FIG. 17 engaged to components of the anchor device of FIG. 2.

In use, the bone screw and sleeve assembly of FIG. 8e is provided together with one or more suitably sized rods 12 and a cap 70 so that a spinal fixation system 10 may be implanted into a patient. The surgeon may insert the bone screw assembly with a suitable screw inserter 140 as shown, for example, in FIGS. 17-18. The screw inserter 140 includes an outer sleeve 142 and an inner shaft 144 rotatably disposed within the sleeve. As shown in the view of FIG. 18, the end 146 of the outer sleeve 142 is configured to contact the proximal upper surface of the sleeve 60. The outer sleeve 142 is fixed to a handle 150, while the inner shaft is fastened to a tightening knob 152 that is rotatably supported on the handle. The inner shaft 144 includes a pin end 148 that is sized to extend through the bore 57 in the yoke 50 and into the bore 30 at the base of the spherical socket 26. The pin end 148 ensures co-axial alignment of the driving tool 140 and the bone screw threaded shank 22. The inner shaft further includes intermediate threads 149 axially offset from the pin end 148. These threads 149 are arranged to engage the internal threads 56 of the yoke arms 54a, 54b.

The threads 149 on the inner shaft 144 of the tool 140 operate similar to the set screw 80. Specifically, as the threads are driven into the internal threads 56 of the yoke 50, the pin end 148 reacts against the bottom of the bore 30 in the bone screw to generate an upward force on the yoke 50. As the yoke is pushed upward, it pulls the ball insert 40 with it, thereby driving the insert into the spherical socket. When the inner shaft 144 has been fully tightened, the screw inserter tool 140, yoke 50, ball insert 40 and bone screw 20 form a rigid connection. The handle 150 of the outer sleeve 142 may then be used to drive the bone screw into the vertebral bone, either manually or with the assistance of an additional driving tool after a suitable hole has been drilled in the pedicle of a vertebra.

Once the bone screw 20 is threaded in position into the spine, the next step to completing the fixation system, such as system 10 shown in FIG. 1, is to introduce the rod 12 into the yoke 50 of the anchor device 15. The rod may be contoured to match the normal curvature of the spine, either in lordosis or kyphosis depending upon the instrumented vertebral level. In some cases, the spine exhibits a lateral curvature, such as scoliosis, that is preferably corrected, at least partially, by the fixation system 10. Thus, in certain cases, the rod 12 itself may be laterally offset from the position of the bone screw engaged within the underlying vertebra. In these cases, the variable angle capabilities of the anchor device of the present disclosed embodiment come into play.

Figure 19:
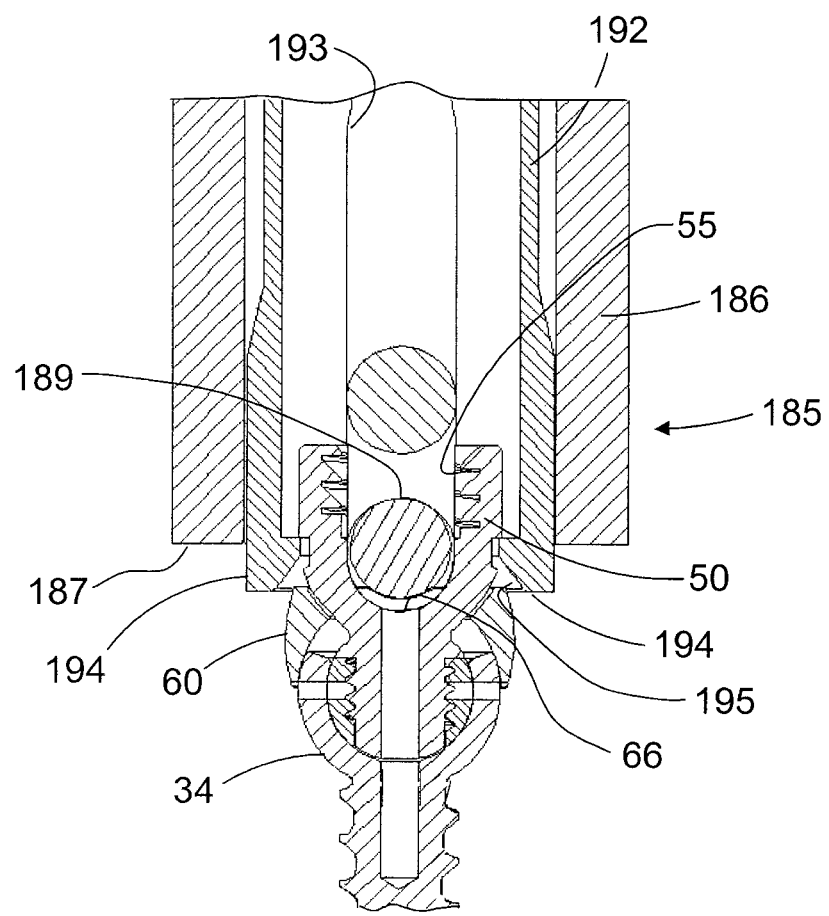
FIG. 19 is a longitudinal cross-sectional view of the lower end of a rod persuader tool engaged to a partially assembled anchor device of FIG. 2.

To accomplish the introduction of the rod 12 into the yoke channel 55 of the yoke 50, a rod persuader tool 185 is provided, as shown in FIG. 19. The rod persuader tool 185 includes an outer tube 186 and an inner tube 192 concentrically disposed within the outer tube for relative axial movement. The outer tube 186 defines a rod notch 189 at its bottom end 187. The inner tube 192 defines a slot 193 that forms legs 194 at the distal end. The legs define an inner shoulder 195 that is configured to suitably engage the partially assembled anchor device. The inner shoulders 195 may engage a groove (not shown) in the outer surface 34 of fastener socket 26. In another embodiment, the yoke 50 may be modified to have a groove (not shown) that may be engaged by the inner shoulders 195. In either embodiment, the legs 194 are configured to partially encircle and firmly grasp the partially assembled anchor device, while the slot 193 accommodates the initial presence of the rod 12 within the yoke channel 55. A guide pin 190 spans the diameter of the outer tube 186 and fits within the slot 193 to control the relative axial movement between the outer tube 186 and the inner tube 192. A suitable mechanism is provided to move the outer tube 186 downward axially relative to inner tube 192. As the outer tube 186 moves downward, it forces the rod 12 into the yoke channel 55 by lower notch 189 and into the rod groove 66 of the sleeve 60.

With the rod 12 suitably placed into the yoke 50, the spinal fixation device 10 may then be completed. Cap 70 as shown in FIG. 8f is then assembled to the yoke 50, as described above with reference to FIGS. 4-5, to lock the rod 12 relative to the yoke 50 and the yoke 50 relative to the bone fastener 20. It should be appreciated that the spinal fixation device 10 as particularly described herein has the advantage of establishing a low profile, since the outer surface of the screw head 24 may be driven down relatively deeply into the pedicle of the vertebra, while still maintaining swivel movement of the yoke 50 until the set screw 80 is tightened. Furthermore, the relatively large surface area of spherical surface 45 of the ball insert 40 tightly pressed against the interior surface of the screw socket 26 provides for a very rigid construct for locking the polyaxial motion of the yoke 50 relative to the screw 20.

In another embodiment, an anchor device 300, shown in FIGS. 20-23, incorporates a friction member in the form of a spring element 340 disposed between the yoke 330 and the outer sleeve 320. The device 300 is configured similar to the anchor devices described above, including a bone screw 305 in which the head 307 forms a spherical socket to receive a ball insert 310. The yoke 330 includes a threaded stem 332 to engage the ball insert within the head of the bone screw, in the manner previously described. As explained above with respect to the embodiment of FIG. 20, it is desirable to provisionally maintain the yoke in a predetermined orientation with respect to the bone screw. The friction member of this embodiment provides a static friction force that is a function of the threaded engagement between the yoke and the ball insert. In other words, as the yoke stem is tightened into the ball insert, the static friction force generated by the spring element 340 increases, thereby increasing the force temporarily holding the yoke in position relative to the fastener.

In the embodiment shown in FIG. 20, the spring element 340 is in the form of a wave washer or wave spring disposed between the lower surface 334 of the yoke and an opposing surface of the outer sleeve 320. As shown in detail in FIGS. 21*a*-21*b*, the spring element 340 includes a ring-shaped body 341 having an outer edge 342 and an inner edge 344. The spring element is bent along one axis to form an apex 346 that is offset or in a different plane than opposite portions 348. The spring element thus operates as a wave spring in that a force F applied at the apex 346 produces reaction forces R at the opposite portions 348, as depicted in FIG. 21*b*.

The function of this reaction force R is illustrated in FIG. 22. The stem 332 of the yoke 330 extends through the center opening 345 of the spring element 340 to threadedly engage the ball insert 310 in the manner described above. The outer sleeve 320 is captured between the yoke and the head 307 of the bone screw 305, also as described above. As the yoke stem is threaded into the ball insert, the lower surface 334 of the yoke bears against the inner edge 344 of the spring element. Thus, the downward force F' exerted by the yoke as it is threaded into the ball insert produces the force F on the apex 346 of the spring element. The resulting reaction force R is exerted by the opposite portions 348 of the spring element against an inner surface 327 of a cylindrical cavity 326 formed in the outer sleeve 320. This reaction force R increases the static friction force between the ring body 341 and the outer sleeve 320, as well as between the ring body and the yoke 330. It can also be appreciated that a commensurate static friction force is produced at the interface between the yoke lower surface 334 and the inner edge 344 of the spring washer. Thus, the presence of the wave spring 340 provides an adjustable friction force between the yoke and the outer sleeve to temporarily fix the relative orientation between the two components.

In addition, the downward force F bears down on the outer sleeve 320 and more particularly on the lower surface 322 of the inner sleeve to press against the outer surface 308 of the head 307 of the bone screw. This pressure helps hold the position of the outer sleeve relative to the bone screw. Thus, the sum of the forces generated by the spring element 340 provisionally holds the yoke and outer sleeve in a predetermined position by loosely tightening the yoke stem into the ball insert. The amount of reaction force R exerted by the spring element, and therefore the amount of static friction force produced by the element, is a function of how far the yoke stem is threaded into the ball insert.

The static friction force produced by the spring element 340 can be manually overcome by pressure against the yoke 330, such as by pushing the top of the yoke laterally to adjust its angular orientation relative to the bone screw. When the lateral pressure is removed, the static friction will hold the yoke in its new position. Thus, the spring element 340 allows the surgeon to provisionally position the yoke as the fixation construct is assembled in situ. Once the yoke has been properly positioned to receive a spinal rod, for instance, the yoke can be fully tightened into the ball insert to clamp the components of the entire anchor device 300 together.

In order to accommodate the spring element 340 the outer sleeve 320 may be modified from the configuration of the prior disclosed embodiments. The lower surface 322 may have the same configuration for engaging the outer surface 308 of the bone screw head 307. The upper surface 324 is abbreviated by the addition of the cylindrical cavity 326 that is sized to receive the ring body 341 of the spring element. However, the upper surface 324 serves the same function as in the previous embodiments. Specifically, the lower surface 334 of the yoke bears against the upper surface 324 of the sleeve as the yoke stem is fully tightened into the ball insert 310. When the yoke stem is fully tightened, the spring element 340 becomes essentially superfluous. The final clamping of the components of the anchor device 330 is thus accomplished by the interaction of the ball insert, the inner and outer surfaces of the bone screw head, the upper and lower surfaces of the outer sleeve and the lower surface of the yoke, all as described above.

It can be appreciated that the spring element permits adjustment of the static friction force operable to hold the yoke in position relative to the fastener. Tightening the yoke into the ball insert increases the static friction force, while loosening the yoke decreases the force. The friction force can be adjusted as necessary by the surgeon.

In the embodiment illustrated in FIG. 22, the reaction force R is exerted essentially parallel to the longitudinal axis of the construct against the surface 327 of the cylindrical cavity 326. In an alternative embodiment, the outer sleeve 320 can be modified to remove the upper portion 320' of the sleeve, with the surface 327 essentially forming the top of the sleeve. In this alternative embodiment, the cavity 326 is essentially eliminated. The spring element will nonetheless be readily retained when the components are initially assembled, since the washer-like configuration of the element 340 allows the yoke stem 322 to be threaded through the center opening 345 in the element.

In another embodiment, the cavity 326 is sized so that the reaction force R is a generally radial force, as shown in FIG. 23. In this version, the opposite portions 348 of the spring element bear against the cylindrical wall 328 of the cavity. Although the reaction force is radial, rather than axial as shown in FIG. 22, a static friction force still arises between the washer and the sleeve that provides the same temporary holding force.

In a specific embodiment, the ring body 341 of the spring element can be formed of a medical grade titanium alloy, such as Ti-6Al-4V. The ring may be 0.020 in. thick with an outer diameter of 0.533 in. and an inner diameter of 0.493 in. The ring body may be bent so that the apex 346 is offset from the outer portions 348 by about 0.080 in.

In the illustrated embodiment, the wave spring configuration of the spring element 340 contemplates one bend at the apex 346 with two opposite portions 348. With this embodiment, the reaction force R is exerted at only two diametrically opposite locations within the cavity 348 of the outer sleeve 340. In alternative embodiments, multiple bends are contemplated to produce multiple undulations around the perimeter of the ring body 341. These multiple undulations result in multiple contact points between the spring element and the cavity 348 of the outer sleeve, and therefore multiple locations at which the reaction force R is applied.

In addition, the anchor device 300 may also be formed to provide for insertion into or removal from a bone. A central bore 352 may be formed through yoke 330, the bore 352 opening at the U-shaped channel at its upper end and opening at the bottom of threaded portion 332 at its lower end. Formed into the lower spherical surface of the head 307 of bone screw 305 is a recess 354, configured preferably to have a Torx shape, although other suitable configurations may be also be used. Recess 354 aligns with bore 352 when the yoke 330 is oriented generally vertically along the axis of bone screw 305 so that a suitable tool, such as a Torx wrench, may be introduced through bore 352 and engage recess 354 to enable implantation of the bone screw 305 into or removal from a bone.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An anchor device for anchoring an elongated rod to the spine, comprising:
    a fastener having a bone engaging portion and a head, said head defining a socket and having a curved outer surface;
    an insert captively retained in said socket and configured for swiveling therein;
    a yoke having a top surface and a rod receiving channel therein, said yoke including a pair of spaced upstanding arms defining said channel, said arms being internally threaded, said yoke being coupled to said insert for articulating movement relative to said fastener, said yoke including a lower surface facing said outer surface of said head of said fastener;
    a sleeve coupled to and extending at least partially around said yoke and having a top surface and a curved inner lower surface configured to be supported by said curved outer surface of said head for common swivel movement of said sleeve and said yoke relative to said fastener head, said top surface of said sleeve being disposed between the top surface of said yoke and the curved outer surface of said fastener;
    a friction member disposed between said yoke and said sleeve and supported by said sleeve for applying a static friction force between said sleeve and said fastener to frictionally maintain said yoke in a movable position relative to said fastener, said friction member including a spring element; and
    a threaded tightening element in threaded engagement with the threaded arms of said yoke for securing said elongate rod within said yoke while overcoming said static force and locking said yoke relative to said fastener.

2. The anchor device of claim 1, wherein said spring element is a wave spring.

3. The anchor device of claim 1, wherein said tightening element is an externally threaded set screw cooperating with said yoke to contact and exert a securing force against said elongate rod.

4. An anchor device for anchoring an elongated rod to the spine, comprising:
    a fastener having a bone engaging portion and a head, said head defining a socket and having a curved outer surface;
    an insert captively retained in said socket and configured for swiveling therein, said insert including an outer surface, one portion of which is spherical and another portion of which is cylindrical;
    a yoke having a top surface and a rod receiving channel therein, said yoke including a pair of spaced upstanding arms defining said channel, said arms being internally threaded, said yoke being coupled to said insert for articulating movement relative to said fastener, said yoke including a lower surface facing said outer surface of said head of said fastener;
    a sleeve coupled to and extending at least partially around said yoke and having a top surface and a curved inner lower surface configured to be supported by said curved outer surface of said head for common swivel movement of said sleeve and said yoke relative to said fastener head, said top surface of said sleeve being disposed between the top surface of said yoke and the curved outer surface of said fastener;
    a friction member disposed between said yoke and said sleeve and supported by said sleeve for applying a static friction force between said sleeve and said fastener to frictionally maintain said yoke in a movable position relative to said fastener; and
    a threaded tightening element in threaded engagement with the threaded arms of said yoke for securing said elongate rod within said yoke while overcoming said static force and locking said yoke relative to said fastener.

5. The anchor device of claim 4, wherein said friction member includes a spring element.

6. The anchor device of claim 5, wherein said spring element is a wave spring.

7. The anchor device of claim 4, wherein said tightening element is an externally threaded set screw cooperating with said yoke to contact and exert a securing force against said elongate rod.

* * * * *